US012653889B2

(12) United States Patent
Chung et al.

(10) Patent No.: US 12,653,889 B2
(45) Date of Patent: Jun. 16, 2026

(54) COMPOSITION FOR PREVENTING OR TREATING EXTRAHEPATIC BILE DUCT CANCER

(71) Applicant: SMT BIO CO., LTD., Seoul (KR)

(72) Inventors: Yong-Yoon Chung, Seoul (KR); Jung-Min Im, Gwangmyeong-si (KR); In-Hye Jung, Seoul (KR)

(73) Assignee: SMT BIO CO., LTD., Seoul (KR)

( * ) Notice: Subject to any disclaimer, the term of this patent is extended or adjusted under 35 U.S.C. 154(b) by 850 days.

(21) Appl. No.: 17/917,854

(22) PCT Filed: Jan. 13, 2022

(86) PCT No.: PCT/KR2022/000634
§ 371 (c)(1),
(2) Date: Oct. 7, 2022

(87) PCT Pub. No.: WO2022/215840
PCT Pub. Date: Oct. 13, 2022

(65) Prior Publication Data
US 2024/0350541 A1 Oct. 24, 2024

(30) Foreign Application Priority Data
Apr. 6, 2021 (KR) ........................ 10-2021-0044391

(51) Int. Cl.
| | |
|---|---|
| *A61K 40/42* | (2025.01) |
| *A61K 35/17* | (2025.01) |
| *A61K 39/395* | (2006.01) |
| *A61K 40/15* | (2025.01) |
| *A61P 35/00* | (2006.01) |

(52) U.S. Cl.
CPC ............ *A61K 40/421* (2025.01); *A61K 35/17* (2013.01); *A61K 39/3955* (2013.01); *A61K 40/15* (2025.01); *A61P 35/00* (2018.01); *A61K 2239/31* (2023.05)

(58) Field of Classification Search
CPC ...... A61K 40/421; A61K 35/17; A61K 40/15; A61K 39/395; A61K 2300/00; A61P 35/00
See application file for complete search history.

(56) References Cited

U.S. PATENT DOCUMENTS 9,834,753 B2 * 12/2017 Min ........................ A61P 27/02

FOREIGN PATENT DOCUMENTS

KR 10-2019-0118788 A 10/2019

OTHER PUBLICATIONS

Gonzalez. Mod Pathol; 29:1358-1369. (Year: 2016).*
Jung. in vivo; 32:771-781. (Year: 2018).*
Clinical Trial No. NCT03937895. Record History; ver. 3: Jan. 13, 2020. (Year: 2020).*
Chung. Abstract CT171: Combinatorial allogeneic NK cell therapy with Pembrolizumab for cholangiocarcinoma; interim report of open label Phase1/2a study. Cancer Res, 81(13_Supplement): CT171. (Year: 2021).*
Heipertz. Current Perspectives on "Off-The-Shelf" Allogeneic NK and CAR-NK Cell Therapies. Front Immunol; 12:72135. (Year: 2021).*
NHS Inform, Bile Duct Cancer. (Year: 2024).*
Internet Webpage Archive, ClinicalTrials.gov, NCT03937895, 'Allogeneic NK Cell ("SMT-NK") in Combination With Pembrolizumab in Advanced Biliary Tract Cancer', Jan. 13, 2020, pp. 1-13.
Satoru Saito, et al., Ex Vivo Generation of Highly Purified and Activated Natural Killer Cells from Human Peripheral Blood, Human Gene Therapy Methods, Aug. 2013, pp. 241-252, vol. 24.
Mao Lin, et al., 'Pembrolizumab plus allogeneic NK cells in advanced non-small cell lung cancer patients', The Journal of Clinical Investigation, May 2020, pp. 2560-2569, vol. 130.
Emilien Loeuillard, et al., 'Immunobiology of cholangiocarcinoma', JHEP Reports, 2019, pp. 297-311, vol. 1.
International Search Report for PCT/KR2022/000634 dated Apr. 20, 2022.

* cited by examiner

*Primary Examiner* — Daniel E Kolker
*Assistant Examiner* — Maureen Varina Driscoll
(74) *Attorney, Agent, or Firm* — Sughrue Mion, PLLC

(57) ABSTRACT

The present invention relates to a pharmaceutical composition for preventing or treating extrahepatic bile duct cancer containing, as active ingredients, natural killer (NK) cells and an anti-PD-1 antibody.

6 Claims, 1 Drawing Sheet

9 cycles
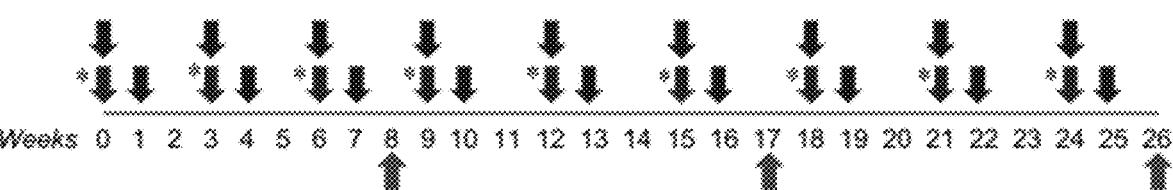

COMPOSITION FOR PREVENTING OR TREATING EXTRAHEPATIC BILE DUCT CANCER

CROSS REFERENCE TO RELATED APPLICATIONS

This application is a National Stage of International Application No. PCT/KR2022/000634 filed Jan. 13, 2022, claiming priority based on Korean Patent Application No. 10-2021-0044391 filed Apr. 6, 2021, the entire disclosures of which are incorporated herein by reference.

TECHNICAL FIELD

The present invention relates to a composition capable of effectively preventing or treating bile duct cancer, particularly extrahepatic bile duct cancer.

BACKGROUND ART

Bile duct cancer is a cancer that occurs in the bile duct that carries bile produced in the liver to the duodenum. Bile is produced by liver cells, comes out of the liver, and is discharged through the papilla of the duodenum. Bile ducts are divided into intrahepatic bile ducts that pass through the liver and extrahepatic bile ducts that exit the liver and extend to the duodenum. Bile duct cancer that occurs in the bile ducts is a tumor composed of cells resembling the epithelium of the bile ducts, and is divided into intrahepatic bile duct cancer and extrahepatic bile duct cancer according to the anatomical location of occurrence. Intrahepatic bile duct cancer is further divided into peripheral cholangiocarcinoma and hilar cholangiocarcinoma, and extrahepatic bile duct cancer is further divided into upper (proximal), middle, and lower (distal) bile duct cancers according to the site of occurrence, and there are differences in clinical features, treatment methods and prognosis.

Bile duct cancer generally occurs more often in the age group over 60 years of age and occurs 1.3 times more in men than in women. Symptoms thereof vary depending on the location of the tumor and the degree of invasion of the tumor. In the initial stage, most patients have no symptoms, but when the bile duct is blocked by the tumor, painless jaundice and jaundice urine (dark brown urine) appear most commonly, and in addition, there may be symptoms such as itchy skin, abdominal pain, weight loss, fever, gray stool, and digestive problems.

Since bile duct cancer does not show any characteristic symptoms until it is significantly advanced, it is difficult to diagnose early, and at the time of diagnosis, radical resection thereof is often impossible because the bile duct cancer invades surrounding major organs. A treatment method for such bile duct cancer varies depending on the location and degree of progression of the cancer. The only treatment for the cure of bile duct cancer is surgical resection, but at the time of diagnosis, bile duct cancer is found to be advanced in more than two-thirds of patients, and thus radical resection thereof is often difficult. More than 80% of bile duct cancer patients, including patients who recur after surgery, receive chemotherapy. To date, gemcitabine is known to be the most effective for bile duct cancer, but the therapeutic effect thereof is only insignificant compared to the therapeutic effects on other cancers, and an effective treatment method for bile duct cancer is required.

Meanwhile, natural killer (NK) cells are known to be involved in innate immunity to remove pathogens and cancer cells, and release interferon-gamma (IFN-$\gamma$), tumor necrosis factor-alpha (TNF-$\alpha$), macrophage inflammatory protein-1$\beta$ (MIP-1$\beta$) and other substances that mediate adaptive immunity. When NK cells meet other cells, the MHC of the NK cells sends a signal to the inside of the NK cells through molecular action if the other cells are cancer cells with no MHC class I or virus-infected cells with MHC class I abnormalities. Thus, NK cells have a system that attacks these abnormal cells. However, it has been reported that the function and differentiation potential of these NK cells are defective in several types of cancer, indicating that there is a close correlation between the survival of cancer cells and the activity of NK cells. Therefore, various studies have been conducted to increase the number or activity of NK cells for cancer immunotherapy, but no satisfactory study results have been obtained yet.

DISCLOSURE

Technical Problem

An object of the present invention is to provide a pharmaceutical composition for preventing or treating bile duct cancer, particularly extrahepatic bile duct cancer.

Another object of the present invention is to provide a method for preventing or treating bile duct cancer, particularly extrahepatic bile duct cancer.

However, objects to be achieved by the present invention are not limited to the objects mentioned above, and other objects not mentioned herein will be clearly understood by those of ordinary skill in the art from the following description.

Technical Solution

Hereinafter, various embodiments described herein will be described with reference to figures. In the following description, numerous specific details are set forth, such as specific configurations, compositions, and processes, etc., in order to provide a thorough understanding of the present invention. However, certain embodiments may be practiced without one or more of these specific details, or in combination with other known methods and configurations. In other instances, known processes and preparation techniques have not been described in particular detail in order to not unnecessarily obscure the present invention. Reference throughout this specification to "one embodiment" or "an embodiment" means that a particular feature, configuration, composition, or characteristic described in connection with the embodiment is included in at least one embodiment of the present invention. Thus, the appearances of the phrase "in one embodiment" or "an embodiment" in various places throughout this specification are not necessarily referring to the same embodiment of the present invention. Additionally, the particular features, configurations, compositions, or characteristics may be combined in any suitable manner in one or more embodiments.

Unless otherwise defined in the specification, all the scientific and technical terms used in the specification have the same meanings as commonly understood by those skilled in the technical field to which the present invention pertains.

An embodiment of the present invention is directed to a pharmaceutical composition for preventing or treating extrahepatic bile duct cancer containing, as active ingredients, natural killer (NK) cells and an anti-PD-1 antibody.

In the present invention, the natural killer cells may be obtained by the steps described below.

1) Step of Obtaining Peripheral Blood Mononuclear Cells

In the present invention, the natural killer cells may be obtained from healthy human blood, for example, whole blood, umbilical cord blood, bone marrow, or peripheral blood, preferably peripheral blood.

In the present invention, a step of isolating and obtaining peripheral blood mononuclear cells (PBMCs) from the peripheral blood obtained as described above may be performed.

In the present invention, the peripheral blood mononuclear cells (PBMCs) are mononuclear cells isolated from the peripheral blood of a mammal, preferably a human, and mainly include immune cells such as B cells, T cells and natural killer cells, and granulocytes such as basophils, eosinophils and neutrophils. The PBMCs may be prepared by a conventional manufacturing method from peripheral blood collected from a living body. Preferably, the PBMCs may be isolated from peripheral blood by specific gravity centrifugation method using Ficoll.

2) Step of Removing CD3$^+$ T Cells

In the present invention, a step of removing CD3$^+$ T cells from the isolated peripheral blood mononuclear cells may be performed. In the present invention, the method for removing the CD3$^+$ T cells is not particularly limited, but may be performed using a commercially available immunomagnetic separation product, for example, MACSxpress (Milteyi Biotec, Germany).

3) Step of Culturing Cells in Culture Medium Containing Cytokine

In the present invention, a step of culturing the peripheral blood mononuclear cells, from which the CD3$^+$ T cells have been removed as described above, may be performed in a culture medium containing a cytokine.

As used herein, the term "cytokine" refers to an immune-activating cytokine that may be used to induce natural killer cells from peripheral blood mononuclear cells. In one embodiment of the present invention, the cytokine may be, for example, IL-2, IL-15, IL-21, Flt3-L, SCF, IL-7, IL-12, IL18, or a mixture of two or more thereof. In particular, IL-2, IL-15 or IL-21 is known as a cytokine having an excellent effect on differentiation into natural killer cells and expansion thereof, and thus is preferably used. Most preferably, IL-2 may be used.

For the purposes of the present invention, the cytokine is preferably contained in an amount of 500 to 1,500 IU/ml, more preferably 800 to 1,200 IU/ml.

In the present invention, the culture medium may be AlyS505NK-AC (Cat. #01600P02), AlyS505NK-AC1000 (Cat. #01610P02), AlyS505NK-EX (Cat. #01400P10) or AlyS505NK-EX1000 (Cat. #01410P10) culture medium from Cell Science & Technology Institute Inc. (CSTI), without being limited thereto.

In addition, in the present invention, the culturing may be performed for 10 to 25 days. In a preferred embodiment of the present invention, the peripheral blood mononuclear cells from which CD3$^+$ T cells have been removed may preferably be cultured in a T75 flask containing 10 to 30 ml of culture medium for 5 to 7 days, and then transferred to and further cultured in a T175 flask for 7 to 14 days, without being limited thereto.

In the present invention, the culturing may be performed using a stationary culture or suspension culture method. As used herein, the term "stationary culture" means culturing in an incubator in a stationary state without agitation or shaking, and the term "suspension culture" means culturing cells in a suspended state by aeration or agitation without attaching the cells to the bottom or side of a reactor. In addition, the reactor for stationary culture and the reactor for suspension culture may be the same as or different from each other. For example, when the reactor for stationary culture and the reactor for suspension culture are the same, stationary culture may be performed in the same reactor, and then suspension culture may be performed in the reactor by additionally supplying a medium containing necessary nutrients such as cytokines. When different kinds of reactors are used, stationary culture may be performed in one reactor, and then the culture may be transferred to another reactor for suspension culture and subjected to suspension culture.

The composition of the present invention may contain the natural killer cells in an amount of $1 \times 10^4$ cells/kg or more, $1 \times 10^5$ cells/kg or more, $3 \times 10^5$ cells/kg or more, $1 \times 10^6$ cells/kg or more, $3 \times 10^6$ cells/kg or more, $6 \times 10^6$ cells/kg or more, or $1 \times 10^7$ cells/kg or more, and $1 \times 10^{10}$ cells/kg or less, preferably $1 \times 10^6$ to $1 \times 10^7$ cells/kg, more preferably $1 \times 10^6$ to $5 \times 10^6$ cells/kg, most preferably $3 \times 10^6$ cells/kg, without being limited thereto.

In the present invention, the anti-PD-1 antibody may be pembrolizumab, nivolumab, pidilizumab, AMP 514 (Amplimmune), PDR-001 (Novartis), MEDI-0690 (also known as AMP-514; MedImmune LLC), SHR-1210 (Incyte Corp.), REGN-2810 (Regeneron Pharmaceuticals, Inc.), PF-06801591 (Pfizer), TSR-042 (also known as ANB011; Tesaro, Inc.), BGB-A317 (BeiGene, Ltd.), or JS001 (Shanghai Junshi Bioscience Co., Ltd.). Preferably, the anti-PD-1 antibody may be pembrolizumab.

In the present invention, "pembrolizumab" is commercially available under the trade name of Keytruda® and corresponds to an immune checkpoint inhibitor. Pembrolizumab is a monoclonal antibody designed to bind to a receptor called PD-1 that is expressed by immune cells such as T cells. The PD-1 receptor was first discovered in 1992, is involved in apoptosis, and is known to be expressed in T cells, B cells, monocytes, and antigen-presenting cells. According to recent reports, the PD-1 receptor is known to be expressed also in natural killer cells. This receptor may bind to the PD-L1 and PD-L2 receptors overexpressed by cancer cells or antigen-presenting cells. This process, which occurs in the process in which T cells or natural killer cells infiltrate, recognize and destroy cancer cells, induces immunosuppression and eventually fails to destroy cancer cells.

The composition of the present invention may contain the anti-PD-1 antibody in an amount of 10 to 1,000 mg, preferably 100 to 1,000 mg, more preferably 200 to 500 mg, most preferably 200 mg or 400 mg, without being limited thereto.

In the present invention, the extrahepatic bile duct cancer may be upper (proximal), middle or lower (distal) bile duct cancer.

In the present invention, the extrahepatic bile duct cancer may be one in which the expression level of PD-L1 (programmed cell death-ligand 1) protein or a gene encoding the protein is 5 to 50%, preferably 30 to 50%. Here, the expression level of the PD-L1 protein or the gene encoding the protein may be a combined positive score (CPS) represented by the following Equation 1, without being limited thereto:

$$\text{CPS (\%)} = (\text{number of PD-L1 positive tumor cells, lymphocytes or macrophages in sample}) / (\text{number of live tumor cells in sample}) \times 100 \quad \text{[Equation 1]}$$

In the present invention, the "PD-L1 (programmed cell death-ligand 1)" is a protein located on the surface of cancer cells or in hematopoietic cells. It is also called CD274 or B7-H1. When the protein PD-L1 or PD-L2 on the surface of cancer cells binds to the protein PD-1 on the surface of T cells, the T cells cannot attack the cancer cells. An immune anticancer drug binds to the PD-1 receptor on T cells and inhibits the evasion function of cancer cells. This corresponds to the principle that Keytruda (MSD) or Opdivo works.

Examples of cancer to be treated according to the present invention include not only extrahepatic bile duct cancer, but also drug-resistant extrahepatic bile duct cancer, and cancer that has recurred or metastasized from the extrahepatic bile duct cancer. More specifically, the cancer may be extrahepatic bile duct cancer resistant to at least one of gemcitabine and cisplatin drugs, or may be extrahepatic bile duct cancer that has recurred or metastasized after treatment with the drug after diagnosis.

As used herein, the term "prevention" or "preventing" refers to any action of inhibiting or delaying extrahepatic bile duct cancer disease by administration of the pharmaceutical composition.

As used herein, the term "treatment" or "treating" refers to any action of alleviating or curing the symptoms of extrahepatic bile duct cancer by administration of the pharmaceutical composition.

In the present invention, the pharmaceutical composition may be in the form of capsules, tablets, granules, injections, ointments, powders or beverages, and the pharmaceutical composition may be for administration to humans.

For use, the pharmaceutical compositions of the present invention may be formulated as oral dosage forms, such as powders, granules, capsules, tablets or aqueous suspensions, external dosage forms, suppositories, and sterile injectable solutions according to conventional methods, without being limited thereto. The pharmaceutical composition of the present invention may contain pharmaceutically acceptable carriers. Pharmaceutically acceptable carriers that may be used for oral administration include binders, lubricants, disintegrants, excipients, solubilizers, dispersing agents, stabilizers, suspending agents, colorants, fragrances, etc. For injection, buffers, preservatives, analgesic agents, solubilizers, isotonic agents, stabilizers, etc., may be used, and for topical administration, bases, excipients, lubricants, preservatives, etc. may be used. The pharmaceutical composition of the present invention may be prepared as various formulations by mixing with the pharmaceutically acceptable carriers as described above. For example, for oral administration, the pharmaceutical composition may be formulated in the form of tablets, troches, capsules, elixirs, suspensions, syrups, wafers, etc., and for injection, it may be formulated as unit dosage ampoules or multi-dose vials. In addition, the pharmaceutical composition of the present invention may be formulated as solutions, suspensions, tablets, capsules, sustained-release preparations, or the like.

Meanwhile, examples of carriers, excipients and diluents suitable for formulation include lactose, dextrose, sucrose, sorbitol, mannitol, xylitol, erythritol, maltitol, starch, gum acacia, alginate, gelatin, calcium phosphate, calcium silicate, cellulose, methyl cellulose, microcrystalline cellulose, polyvinyl pyrrolidone, water, methylhydroxy benzoate, propylhydroxy benzoate, talc, magnesium stearate, mineral oil and the like. In addition, the pharmaceutical composition may further contain a filler, an anticoagulant, a lubricant, a wetting agent, a fragrance, an emulsifier, a preservative, etc.

The routes of administration of the pharmaceutical composition according to the present invention include, but are not limited to, oral, intravenous, intramuscular, intra-arterial, intra-marrow, intrathecal, intracardiac, transdermal, subcutaneous, intraperitoneal, intranasal, intestinal, local, sublingual or intrarectal routes. Oral or parenteral administration is preferred.

In the present invention, "parenteral" includes subcutaneous, transdermal, intravenous, intramuscular, intra-articular, intra-synovial, intrasternal, intrathecal, intra-lesional and intra-cranial injection or infusion techniques. The pharmaceutical composition of the present invention may also be formulated as suppositories for intrarectal administration.

The pharmaceutical composition of the present invention may vary depending on various factors, including the activity of a specific compound used, the patient's age, body weight, general health, sex, diet, the period of administration, the route of administration, excretion rate, the drug content, and the severity of a specific disease to be prevented or treated. The dose of the pharmaceutical composition may be suitably selected by a person skilled in the art depending on the patient's condition, body weight, the severity of the disease, the form of drug, and the route and period of administration, and may be 0.0001 to 50 mg/kg/day or 0.001 to 50 mg/kg/day. The pharmaceutical composition may be administered once or several times a day. The dose is not intended to limit the scope of the present invention in any way. The pharmaceutical composition according to the present invention may be formulated as pills, sugar-coated tablets, capsules, liquids, gels, syrups, slurries, or suspensions.

Another embodiment of the present invention is directed to a method for preventing or treating extrahepatic bile duct cancer comprising a step of administering effective amounts of natural killer (NK) cells and an anti-PD-1 antibody to a subject.

In the present invention, the "subject" may be a mammal or non-mammal having or being at risk of developing extrahepatic bile duct cancer. Here, examples of the mammal include, but are not limited to, humans, non-human primates such as chimpanzees, other ape or monkey species; farm animals such as cattle, horses, sheep, goats, and pigs; domestic animals such as rabbits, dogs or cats; and laboratory animals such as rodents, for example, rats, mice or guinea pigs. In addition, examples of the non-mammal that may be used in the present invention include, but are not limited to, birds or fish.

In the present invention, details regarding the method for obtaining the natural killer cells overlap with those described above with respect to the pharmaceutical composition, and thus detailed description thereof will be omitted to avoid excessive complexity of the specification.

In the method of the present invention, the natural killer cells may be administered to the subject in an amount of $1 \times 10^4$ cells/kg or more, $1 \times 10^5$ cells/kg or more, $3 \times 10^5$ cells/kg or more, $1 \times 10^6$ cells/kg or more, $3 \times 10^6$ cells/kg or more, $6 \times 10^6$ cells/kg or more, or $1 \times 10^7$ cells/kg or more, and $1 \times 10^{10}$ cells/kg or less, preferably $1 \times 10^6$ to $1 \times 10^7$ cells/kg, more preferably $1 \times 10^6$ to $5 \times 10^6$ cells/kg, most preferably $3 \times 10^6$ cells/kg, without being limited thereto.

In the present invention, the anti-PD-1 antibody may be pembrolizumab, nivolumab, pidilizumab, AMP 514 (Amplimmune), PDR-001 (Novartis), MEDI-0690 (also known as AMP-514; MedImmune LLC), SHR-1210 (Incyte Corp.), REGN-2810 (Regeneron Pharmaceuticals, Inc.), PF-06801591 (Pfizer), TSR-042 (also known as ANB011; Tesaro, Inc.), BGB-A317 (BeiGene, Ltd.), or JS001 (Shanghai Junshi Bioscience Co., Ltd.). Preferably, the anti-PD-1 antibody may be pembrolizumab.

In the method of the present invention, the pembrolizumab may be administered to the subject in an amount of 10 to 1,000 mg, preferably 100 to 1,000 mg, more preferably 200 to 500 mg, most preferably 200 mg or 400 mg in each administration step, without being limited thereto.

In the present invention, the extrahepatic bile duct cancer may be upper (proximal), middle or lower (distal) bile duct cancer.

In the present invention, the extrahepatic bile duct cancer may be one in which the expression level of PD-L1 (programmed cell death-ligand 1) protein or a gene encoding the protein, that is, the combined positive score (CPS) represented by Equation 1, is 5 to 50%, preferably 30 to 50%.

Examples of cancer to be treated according to the present invention include not only extrahepatic bile duct cancer, but also drug-resistant extrahepatic bile duct cancer, and cancer that has recurred or metastasized from the extrahepatic bile duct cancer. More specifically, the cancer may be extrahepatic bile duct cancer resistant to at least one of gemcitabine and cisplatin drugs, or may be extrahepatic bile duct cancer that has recurred or metastasized after treatment with the drug after diagnosis.

In the method of the present invention, the order of administration of the natural killer (NK) cells and the anti-PD-1 antibody is not particularly limited. For example, the natural killer (NK) cells may be administered followed by administration of the anti-PD-1 antibody. Alternatively, the anti-PD-1 antibody may be administered followed by administration of the natural killer (NK) cells. Alternatively, the natural killer cells and the anti-PD-1 antibody may be administered simultaneously.

In the method, the step of administering may comprise a first administration of the natural killer cells and the anti-PD-1 antibody to the subject, followed by a second administration of the natural killer cells to the subject, without being limited thereto.

In the present invention, the second administration may be performed after a period of at least 1 day, preferably at least 3 days, more preferably at least 5 days, and most preferably 7 days, after the first administration.

In the present invention, the second administration may be followed by a drug-free period of at least 1 day, preferably at least 3 days, more preferably at least 5 days, most preferably 7 days.

In the present invention, the cycle of the first and second administrations in the step of administering may be repeated at least 3 times, preferably at least 9 times, more preferably at least 12 times, most preferably at least 24 times, without being limited thereto, and the number of the repeated cycles may be appropriately changed in consideration of the patient's condition, drug efficacy, pathological conditions, and the like.

In the present invention, the natural killer cells and the anti-PD-1 antibody may be administered to the subject by administering pharmaceutical compositions containing them alone or in combination.

In the present invention, the pharmaceutical composition may be in the form of capsules, tablets, granules, injections, ointments, powders or beverages.

For use, the pharmaceutical compositions of the present invention may be formulated as oral dosage forms, such as powders, granules, capsules, tablets or aqueous suspensions, external dosage forms, suppositories, and sterile injectable solutions according to conventional methods, without being limited thereto. The pharmaceutical composition of the present invention may contain pharmaceutically acceptable carriers. Pharmaceutically acceptable carriers that may be used for oral administration include binders, lubricants, disintegrants, excipients, solubilizers, dispersing agents, stabilizers, suspending agents, colorants, fragrances, etc. For injection, buffers, preservatives, analgesic agents, solubilizers, isotonic agents, stabilizers, etc., may be used, and for topical administration, bases, excipients, lubricants, preservatives, etc. may be used. The pharmaceutical composition of the present invention may be prepared as various formulations by mixing with the pharmaceutically acceptable carriers as described above. For example, for oral administration, the pharmaceutical composition may be formulated in the form of tablets, troches, capsules, elixirs, suspensions, syrups, wafers, etc., and for injection, it may be formulated as unit dosage ampoules or multi-dose vials. In addition, the pharmaceutical composition of the present invention may be formulated as solutions, suspensions, tablets, capsules, sustained-release preparations, or the like.

Meanwhile, examples of carriers, excipients and diluents suitable for formulation include lactose, dextrose, sucrose, sorbitol, mannitol, xylitol, erythritol, maltitol, starch, gum acacia, alginate, gelatin, calcium phosphate, calcium silicate, cellulose, methyl cellulose, microcrystalline cellulose, polyvinyl pyrrolidone, water, methylhydroxy benzoate, propylhydroxy benzoate, talc, magnesium stearate, mineral oil and the like. In addition, the pharmaceutical composition may further contain a filler, an anticoagulant, a lubricant, a wetting agent, a fragrance, an emulsifier, a preservative, etc.

The routes of administration of the pharmaceutical composition according to the present invention include, but are not limited to, oral, intravenous, intramuscular, intra-arterial, intra-marrow, intrathecal, intracardiac, transdermal, subcutaneous, intraperitoneal, intranasal, intestinal, local, sublingual or intrarectal routes. Oral or parenteral administration is preferred.

In the present invention, "parenteral" includes subcutaneous, transdermal, intravenous, intramuscular, intra-articular, intra-synovial, intrastemal, intrathecal, intra-lesional and intra-cranial injection or infusion techniques. The pharmaceutical composition of the present invention may also be formulated as suppositories for intrarectal administration.

The pharmaceutical composition of the present invention may vary depending on various factors, including the activity of a specific compound used, the patient's age, body weight, general health, sex, diet, the period of administration, the route of administration, excretion rate, the drug content, and the severity of a specific disease to be prevented or treated. The dose of the pharmaceutical composition may be suitably selected by a person skilled in the art depending on the patient's condition, body weight, the severity of the disease, the form of drug, and the route and period of administration, and may be 0.0001 to 50 mg/kg/day or 0.001 to 50 mg/kg/day. The pharmaceutical composition may be administered once or several times a day. The dose is not intended to limit the scope of the present invention in any way. The pharmaceutical composition according to the present invention may be formulated as pills, sugar-coated tablets, capsules, liquids, gels, syrups, slurries, or suspensions.

Advantageous Effects

When the composition of the present invention is used, it is possible to effectively prevent, alleviate or treat extrahepatic bile duct cancer, and particularly, it is possible to prevent, alleviate or treat extrahepatic bile duct cancer that is resistant to anticancer drugs or has recurred after anticancer therapy.

BRIEF DESCRIPTION OF DRAWINGS

The FIGURE shows a method of administering natural killer cells and pembrolizumab to a patient with extrahepatic bile duct cancer according to an embodiment of the present invention.

BEST MODE

An embodiment of the present invention is directed to a pharmaceutical composition for preventing or treating extrahepatic bile duct cancer containing, as active ingredients, natural killer (NK) cells and an anti-PD-1 antibody.

In the present invention, the anti-PD-1 antibody may be pembrolizumab, nivolumab, pidilizumab, AMP 514 (Amplimmune), PDR-001 (Novartis), MEDI-0690 (also known as AMP-514; MedImmune LLC), SHR-1210 (Incyte Corp.), REGN-2810 (Regeneron Pharmaceuticals, Inc.), PF-06801591 (Pfizer), TSR-042 (also known as ANB011; Tesaro, Inc.), BGB-A317 (BeiGene, Ltd.), or JS001 (Shanghai Junshi Bioscience Co., Ltd.). Preferably, the anti-PD-1 antibody may be pembrolizumab.

In the present invention, the extrahepatic bile duct cancer may be one in which the expression level of PD-L1 (programmed cell death-ligand 1) protein or a gene encoding the protein, preferably the combined positive score (CPS), is 5 to 50%.

MODE FOR INVENTION

Hereinafter, the present invention will be described in more detail with reference to examples. These examples are only for illustrating the present invention in more detail, and it will be apparent to those skilled in the art that the scope of the present invention according to the subject matter of the present invention is not limited by these examples.

Examples

1. Preparation of Natural Killer Cell Therapy Product (SMT-NK Line)

60 ml of blood was collected from the subject's family or a healthy blood donor and then centrifuged using Ficoll-Paque PLUS at 3,000 rpm for 30 minutes, and the peripheral blood mononuclear cell (PBMC) layer was collected. Thereafter, $CD3^+$ T cells were removed from the collected PBMCs using MACSxpress (Milteyi Biotec, Germany), and the PBMCs from which the $CD3^+$ T cells have been removed were washed twice with Dulbecco's phosphate-buffered saline (DPBS). Then, the cells were cultured in a T75 flask containing 20 ml of NK expansion medium (ALyS505NK-IL2 1000 IU/ml, Cell Science & Technology Inst). Fresh medium was added to the IL-2-activated natural killer cells every 3 days, and after 5 to 7 days of culture, the cells were transferred to a T175 flask. Natural killer cell expansion was further performed for 7 to 14 days until the desired cell number was reached, while fresh medium was continuously added. The viability and number of the expanded natural killer cells were measured using a trypan blue counting method and an automatic cell counter.

2. Selection of Patients to be Treated 15 patients, who have been diagnosed with extrahepatic bile duct cancer and intrahepatic bile duct cancer, were selected and subjected to an experiment. However, criteria for patient selection included males and females between the ages of 19 and 80 years old, and patients with a combined positive score (CPS) (corresponding to the level of tumor PD-L1 expression) of 1% or more as determined by immunohistochemical staining (IHC 22C3 pharmDx test), or patients with a MSI-high positive tumor as determined by PCR, or patients with a dMMR** positive tumor as determined by immunohistochemical staining. Table 1 below summarizes the cancer type and combined positive score (CPS) of tumor PD-L1 in the selected patients, and drugs to which the patients were resistant.

TABLE 1

| Patient serial No. | PD-L1 score | Name of diagnosed disease | Drugs to which patients were resistant |
|---|---|---|---|
| 1 | 1 | Extrahepatic bile duct cancer | Gemcitabine, cisplatin, 5-FU |
| 2 | 95 | Extrahepatic bile duct cancer | Gemcitabine, cisplatin, radiotherapy |
| 3 | 5 | Intrahepatic bile duct cancer | Gemcitabine, cisplatin 5-FU, levofolic |
| 4 | 2 | Extrahepatic bile duct cancer | Gemcitabine, cisplatin, 5-FU |
| 5 | 3 | Extrahepatic bile duct cancer | Gemcitabine, cisplatin |
| 6 | 1 | Intrahepatic bile duct cancer | Gemcitabine, cisplatin |
| 7 | 2 | Intrahepatic bile duct cancer | Gemcitabine, cisplatin |
| 8 | 2 | Intrahepatic bile duct cancer | Gemcitabine, cisplatin |
| 9 | 30 | Extrahepatic bile duct cancer | Gemcitabine, cisplatin |
| 10 | 3 | Extrahepatic bile duct cancer | Gemcitabine, cisplatin, 5-FU |
| 11 | 50 | Extrahepatic bile duct cancer | Gemcitabine, cisplatin |
| 12 | 5 | Extrahepatic bile duct cancer | Gemcitabine, cisplatin |
| 13 | 1 | Extrahepatic bile duct cancer | Gemcitabine, cisplatin |
| 14 | 35 | Intrahepatic bile duct cancer | Gemcitabine, cisplatin |
| 15 | 5 | Intrahepatic bile duct cancer | Gemcitabine, cisplatin, 5-FU |

3. Determination of Dosage and Administration Method

To the patients selected as described above, the prepared SMT-NK line (allogeneic blood- derived natural killer cells) and pembrolizumab (Keytruda®) were administered by the method shown in FIGURE. Specifically, the SMT-NK line (blue arrow) was administered intravenously to the patients at a dose of $3 \times 10^6$ (±20%) cells/kg, once a week a total of 48 times, with a drug-free period of one week after two administrations, and pembrolizumab (Keytruda®) (red arrow with an asterisk (* was administered to the patients by intravenous instillation at a dose of 200 mg, once every 3 weeks for a total of 24 times.

4. Evaluation of Treatment Results

While the SMT-NK line and pembrolizumab (Keytruda®) were administered to each patient as described above, computed tomography (CT) was performed every 3 cycles to evaluate the drug efficacy. After a total of 9 cycles (administration of the SMT-NK line for a total of 48 times, and administration of pembrolizumab for a total of 24 times), it was evaluated whether the cancer was in complete response (CR), partial response (PR), stable disease (SD), or progressive disease (PD). The results are shown in Table 2 below.

TABLE 2

| Serial No. | PD-L1 score | Name of diagnosed disease | Drugs to which patients were resistant | Maximum tumor response | Final tumor response |
|---|---|---|---|---|---|
| 1 | 1 | Extrahepatic bile duct cancer | Gemcitabine, cisplatin, 5-FU | SD | PD |
| 2 | 95 | Extrahepatic bile duct cancer | Gemcitabine, cisplatin, radiotherapy | SD | PD |
| 3 | 5 | Intrahepatic bile duct cancer | Gemcitabine, cisplatin 5-FU, levofolic | PD | PD |
| 4 | 2 | Extrahepatic bile duct cancer | Gemcitabine, cisplatin, 5-FU | PD | PD |
| 5 | 3 | Extrahepatic bile duct cancer | Gemcitabine, cisplatin | PD | PD |
| 6 | 1 | Intrahepatic bile duct cancer | Gemcitabine, cisplatin | PD | PD |
| 7 | 2 | Intrahepatic bile duct cancer | Gemcitabine, cisplatin | PD | PD |
| 8 | 2 | Intrahepatic bile duct cancer | Gemcitabine, cisplatin | SD | PD |
| 9 | 30 | Extrahepatic bile duct cancer | Gemcitabine, cisplatin | PR | CR |
| 10 | 3 | Extrahepatic bile duct cancer | Gemcitabine, cisplatin, 5-FU | PR | PD |
| 11 | 50 | Extrahepatic bile duct cancer | Gemcitabine, cisplatin | PR | CR |
| 12 | 5 | Extrahepatic bile duct cancer | Gemcitabine, cisplatin | SD | SD |
| 13 | 1 | Extrahepatic bile duct cancer | Gemcitabine, cisplatin | SD | PD |
| 14 | 35 | Intrahepatic bile duct cancer | Gemcitabine, cisplatin | SD | PD |
| 15 | 5 | Intrahepatic bile duct cancer | Gemcitabine, cisplatin, 5-FU | SD | CR |

As shown in Table 2 above, as a result of administering the natural killer cells and pembrolizumab to 9 patients with extrahepatic bile duct cancer and 6 patients with intrahepatic bile duct cancer, it was confirmed that, in terms of the maximum tumor response, the therapeutic effect was shown in 7 (77.78%) out of the 9 patients with extrahepatic bile duct cancer, whereas only 3 out (50%) of the 6 patients with intrahepatic bile duct cancer showed stable disease (SD). In addition, in terms of the final tumor response, the effective therapeutic effect was shown in 3 (33.33%) out of the 9 patients with extrahepatic bile duct cancer, and 2 out of the 9 patients showed complete response (CR). However, in the case of the patients with intrahepatic bile duct cancer, the therapeutic effect was shown in only one (16.67%) out of the 6 patients, and most (five patients; 83.33%) of the 6 patients showed advanced bile duct cancer. In addition, among all the patients, 3 (75%) out of 4 patients (3 CR and 1 SD) who showed the therapeutic effect corresponded to extrahepatic bile duct cancer, and 2 (66.67%) out of 3 patients who showed complete remission (CR) corresponded to extrahepatic bile duct cancer.

Furthermore, it could be seen found that, among the patients with extrahepatic bile duct cancer, in particular, patients with a PD-L1 combined positive score (CPS) of 5 to 50% showed better therapeutic effects of natural killer cells and pembrolizumab than those having a PD-L1 combined positive score (CPS) out of the above range.

Thereby, it could be confirmed that the therapeutic effects of natural killer cells and pembrolizumab were much better in the patients with extrahepatic bile duct cancer than in the patients with intrahepatic bile duct cancer, and it could be seen that the therapeutic effects of natural killer cells and pembrolizumab were better in patients with a PD-L1 combined positive score (CPS) of 5 to 50%, among the patients with extrahepatic bile duct cancer.

Although the present invention has been described in detail with reference to the specific features, it will be apparent to those skilled in the art that this detailed description is only of a preferred embodiment thereof, and does not limit the scope of the present invention. Thus, the substantial scope of the present invention will be defined by the appended claims and equivalents thereto.

INDUSTRIAL APPLICABILITY

The present invention relates to a composition capable of effectively preventing or treating bile duct cancer, particularly extrahepatic bile duct cancer, and a method of preventing or treating extrahepatic bile duct cancer using the same.

The invention claimed is:
1. A method for treating extrahepatic bile duct cancer comprising a step of administering effective amounts of natural killer (NK) cells and pembrolizumab to a subject in need thereof,
   wherein a combined positive score (CPS) of PD-L1 (programmed cell death-ligand 1) in the extrahepatic bile duct cancer is 30 to 50%,
   wherein the subject has an extrahepatic bile duct cancer resistant to gemcitabine and cisplatin,
   wherein the method comprises a step of obtaining natural killer (NK) cells by culturing peripheral blood mononuclear cells (PBMCs) in a T75 flask containing 500 to 1,500 IU/ml of a cytokine-containing culture medium for 5 to 7 days, and then transferring the cultured cells to a T175 flask, followed by further culturing for 7 to 14 days,
   wherein the step of administering comprises a first administration of the natural killer (NK) cells and the pembrolizumab to the subject, followed by a second administration of the natural killer (NK) cells to the subject, wherein the cycle of the first and the second administrations in the step of administering is repeated at least 3 times.

2. The method of claim 1, wherein the second administration is performed after a period of at least 1 day.

3. The method of claim 1, wherein the peripheral blood mononuclear cells (PBMCs) are those from which $CD^{3+}T$ cells have been removed.

4. The method of claim 1, wherein the natural killer (NK) cells are administered in an amount of $1\times10^4$ cells/kg to $1\times10^{10}$ cells/kg.

5. The method of claim 1, wherein the pembrolizumab is administered in an amount of 10 to 1,000 mg.

6. The method of claim 1, wherein the extrahepatic bile duct cancer is upper (proximal), middle or lower (distal) bile duct cancer.

* * * * *